US009867626B2

(12) United States Patent
Fetzer et al.

(10) Patent No.: US 9,867,626 B2
(45) Date of Patent: Jan. 16, 2018

(54) PUSH BUTTON RONGEUR

(71) Applicant: Boss Instruments, Ltd., Inc., Gordonville, VA (US)

(72) Inventors: Berndt Fetzer, Schaumburg, IL (US); Peter Fetzer, Oehningen-Wangen (DE)

(73) Assignee: BOSS INSTRUMENTS LTD., INC., Gordonsville, VA (US)

( * ) Notice: Subject to any disclaimer, the term of this patent is extended or adjusted under 35 U.S.C. 154(b) by 262 days.

(21) Appl. No.: 14/419,344

(22) PCT Filed: Aug. 1, 2013

(86) PCT No.: PCT/US2013/053192
§ 371 (c)(1),
(2) Date: Feb. 3, 2015

(87) PCT Pub. No.: WO2014/022645
PCT Pub. Date: Feb. 6, 2014

(65) Prior Publication Data
US 2015/0201950 A1    Jul. 23, 2015

Related U.S. Application Data

(60) Provisional application No. 61/679,316, filed on Aug. 3, 2012.

(51) Int. Cl.
A61B 17/16    (2006.01)
A61B 90/00    (2016.01)

(52) U.S. Cl.
CPC ...... A61B 17/1604 (2013.01); A61B 17/1611 (2013.01); A61B 2090/0813 (2016.02)

(58) Field of Classification Search
CPC .................. A61B 17/1604; A61B 17/1611
See application file for complete search history.

(56) References Cited

U.S. PATENT DOCUMENTS

| 3,842,839 A | 10/1974 | Malis et al. |
| 4,499,899 A | 2/1985 | Lyons, III |
| 4,545,374 A | 10/1985 | Jacobson |
| 4,722,338 A | 2/1988 | Wright et al. |
| 4,733,633 A | 3/1988 | Farley |
| 4,770,174 A | 9/1988 | Luckman et al. |
| 4,990,148 A | 2/1991 | Worrick, III et al. |
| 5,009,661 A | 4/1991 | Michelson |

(Continued)

FOREIGN PATENT DOCUMENTS

| CA | 2007589 | 7/1990 |
| CA | 2117220 | 9/1994 |

(Continued)

OTHER PUBLICATIONS

WIPO: International Search Report | International Patent Application No. PCT/US2013/053192 | dated Nov. 29, 2013.

(Continued)

Primary Examiner — Nicholas Woodall
(74) Attorney, Agent, or Firm — Joshua B. Brady; Williams Mullen

(57) ABSTRACT

Disclosed is a Rongeur for surgical use. The disclosed Rongeur has a push button actuator which, upon activation, allows the long parts of the Rongeur to be easily separated for thorough cleaning and sterilization for reuse.

9 Claims, 6 Drawing Sheets

(56) References Cited

U.S. PATENT DOCUMENTS

| | | |
|---|---|---|
| 5,026,375 A | 6/1991 | Linovitz et al. |
| 5,061,269 A | 10/1991 | Muller |
| 5,273,519 A | 12/1993 | Koros et al. |
| 5,312,407 A | 5/1994 | Carter |
| 5,439,464 A | 8/1995 | Shapiro |
| 5,451,227 A | 9/1995 | Michelson |
| 5,484,441 A | 1/1996 | Koros et al. |
| 5,569,258 A | 10/1996 | Gambale |
| 5,584,844 A | 12/1996 | Weisshaupt |
| 5,584,855 A | 12/1996 | Onik |
| 5,653,713 A | 8/1997 | Michelson |
| 5,766,177 A | 6/1998 | Lucas-Dean et al. |
| 5,851,214 A | 12/1998 | Larsen et al. |
| 5,961,531 A | 10/1999 | Weber et al. |
| 6,129,740 A | 10/2000 | Michelson |
| 6,142,997 A | 11/2000 | Michelson |
| 6,200,320 B1 | 3/2001 | Michelson |
| 6,214,010 B1 | 4/2001 | Farley et al. |
| 6,478,805 B1 | 11/2002 | Marino et al. |
| 6,575,977 B1 | 6/2003 | Michelson |
| 6,609,322 B1 | 8/2003 | Michelson |
| 6,638,280 B2 | 10/2003 | Agbodoe |
| 6,685,710 B2 | 2/2004 | Agbodoe et al. |
| 6,695,849 B2 | 2/2004 | Michelson |
| 6,699,254 B1 * | 3/2004 | Tontarra ............ A61B 17/1611 606/83 |
| 6,723,103 B2 | 4/2004 | Edwards |
| 6,991,633 B2 | 1/2006 | Agbodoe |
| 7,011,663 B2 | 3/2006 | Michelson |
| 7,014,638 B2 | 3/2006 | Michelson |
| 7,297,147 B2 | 11/2007 | Michelson |
| 7,615,053 B2 | 11/2009 | McKinley |
| 7,691,107 B2 | 4/2010 | Schneiter |
| 7,922,723 B2 | 4/2011 | Michelson |
| 7,988,699 B2 | 8/2011 | Martz et al. |
| 2001/0005786 A1 | 6/2001 | Michelson |
| 2001/0031221 A1 | 10/2001 | Wu et al. |
| 2003/0069583 A1 | 4/2003 | Agbodoe et al. |
| 2003/0069584 A1 | 4/2003 | Agbodoe |
| 2003/0187450 A1 | 10/2003 | Agbodoe |
| 2003/0216740 A1 | 11/2003 | Michelson |
| 2004/0035903 A1 | 2/2004 | Michelson |
| 2004/0044346 A1 | 3/2004 | Boury |
| 2004/0049200 A1 | 3/2004 | Edwards |
| 2004/0102783 A1 | 5/2004 | Sutterlin, III et al. |
| 2004/0122433 A1 | 6/2004 | Loubens et al. |
| 2004/0186499 A1 | 9/2004 | Michelson |
| 2006/0095043 A1 | 5/2006 | Martz et al. |
| 2006/0122615 A1 | 6/2006 | McKinley |
| 2006/0149271 A1 | 7/2006 | Michelson |
| 2006/0189995 A1 | 8/2006 | Lancial |
| 2007/0093843 A1 | 4/2007 | Schneiter |
| 2008/0255563 A1 | 10/2008 | Farr et al. |
| 2009/0062805 A1 | 3/2009 | Casutt |
| 2009/0309998 A1 | 12/2009 | Grosvenor et al. |
| 2010/0198222 A1 | 8/2010 | Schneiter |
| 2011/0172647 A1 | 7/2011 | Wenzler et al. |
| 2011/0190773 A1 | 8/2011 | Michelson |
| 2011/0213369 A1 | 9/2011 | Weaver |
| 2012/0010622 A1 | 1/2012 | Heinemann |

FOREIGN PATENT DOCUMENTS

| | | |
|---|---|---|
| CA | 2159685 | 4/1996 |
| DE | 43 16 768 A1 | 11/1994 |
| DE | 10 2009 006 689 | 10/2009 |
| EP | 2 213 254 | 8/2010 |
| JP | 2010-035669 | 2/2010 |
| WO | 94/26180 A1 | 11/1994 |
| WO | 95/05123 | 2/1995 |
| WO | 96/14799 | 5/1996 |
| WO | 99/65396 | 12/1999 |
| WO | 2004/049956 | 6/2004 |
| WO | 2006/044920 | 4/2006 |
| WO | 2006/062555 | 6/2006 |
| WO | 2008/039696 | 4/2008 |
| WO | 2008/058070 | 5/2008 |

OTHER PUBLICATIONS

EPO: Extended European Search Report | European Patent Application No. 13825313.3 | dated May 27, 2016.

\* cited by examiner

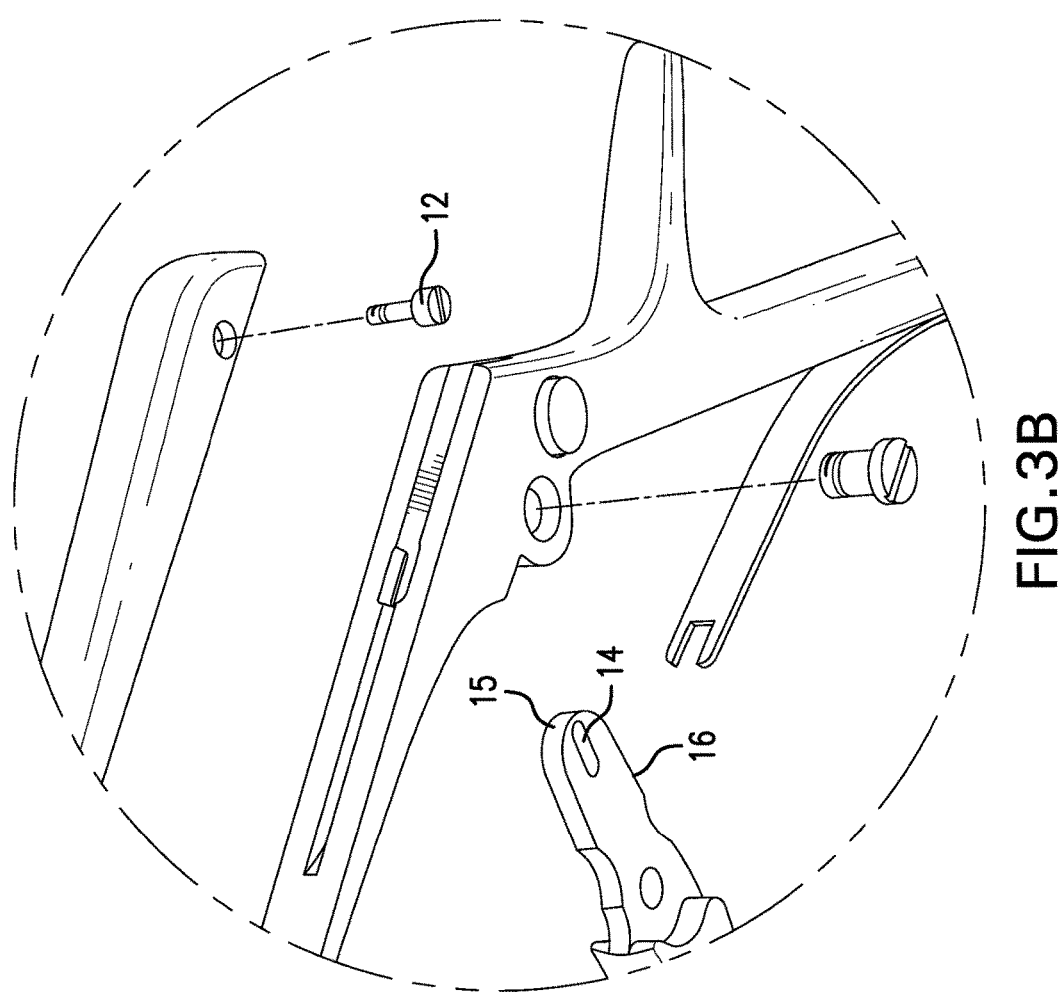

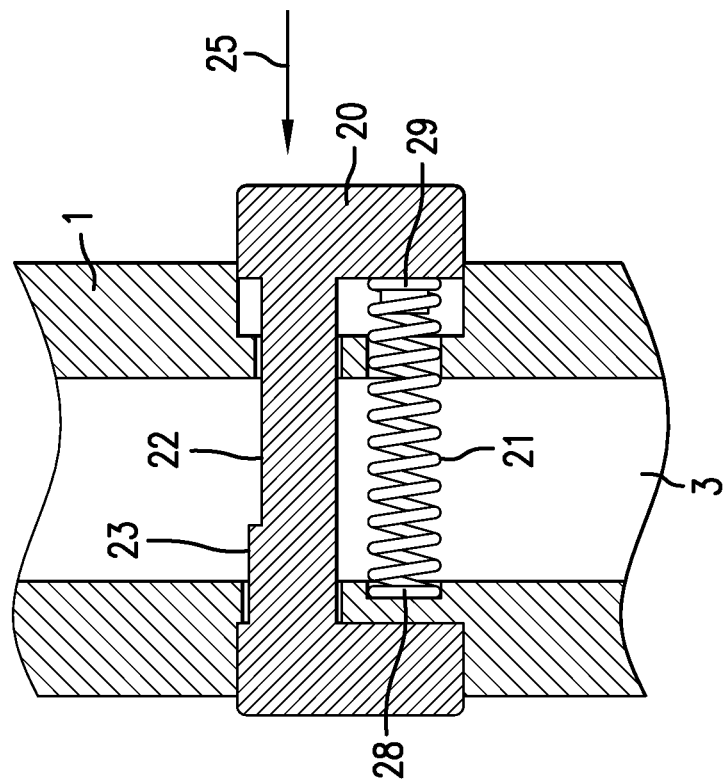
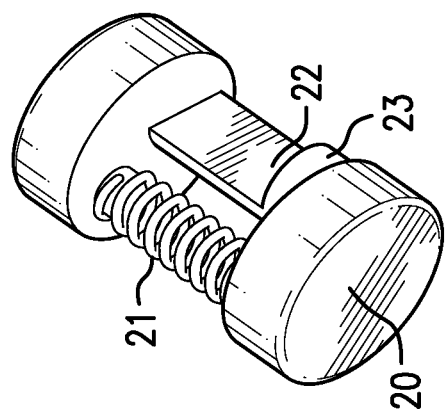

PUSH BUTTON RONGEUR

GOVERNMENT SUPPORT

None.

RELATED APPLICATIONS

None.

FIELD OF THE INVENTION

The present invention relates generally to the field of medical instruments. Specifically, the present invention relates to an improved Rongeur having a push button actuator to allow the separation of its long parts to facilitate improved cleaning and sterilization.

DESCRIPTION OF THE RELATED ART

In surgical procedures, a Rongeur is used to remove a small amount of tissue or bone material. Critical to the reuse of Rongeurs in successive procedures, is the need to thoroughly clean the instrument of biological material and other contamination so as to thoroughly sterilize the instrument. A number of Rongeurs have been developed to facilitate the cleaning and sterilization of their various components. Designs for these Rongeurs include making them able to be disassembled, cleaned and sterilized, and reassembled for subsequent use. This requires skilled technicians and an extended time for cleaning. More recently, a Rongeur has been developed (U.S. Pat. No. 5,961,531, Weber) which allows the long parts of the Rongeur to be totally separated from each other such that the top long part of the Rongeur remains attached at an obtuse angle to the body of the Rongeur by an attachment means. While this is clearly an improvement over Rongeurs requiring disassembly and reassembly, it presents a complex design requiring, among other things, the release of its drive pin from its driving slot.

Accordingly, there is a need for a Rongeur that is simplified in structure with fewer parts, yet facilitates cleaning and sterilization for subsequent use by allowing direct access to the long parts of the Rongeur.

SUMMARY OF THE INVENTION

The present invention is directed to a Rongeur with a simpler, more elegant design with fewer parts which allows direct access to the parts in need of cleaning and sterilization by allowing the separation of those parts with a push button actuator.

In the present disclosure, a Rongeur is presented having a fixed bottom shaft and a movable top shaft (the long parts). The top shaft is slideably connected to and axially aligned with the fixed bottom shaft. The top shaft has a distal end with a cutting portion and a proximal end containing a cavity across which a drive pin is connected. Once the Rongeur is assembled, the drive pin remains captured by the driving hole of the front handle. When the push button actuator is activated, the movable top shaft is retracted slightly to allow the separation of the movable top shaft from the fixed bottom shaft to an acute angle there between. This allows full and direct access to the long parts for cleaning and sterilization.

While the present invention is directed to a more simplified Rongeur requiring fewer parts, while facilitating cleaning and sterilization, it may apply to various other specific types of Rongeurs. Moreover, the present invention also applies to other types of medical instruments that have inaccessible surfaces that are difficult to properly clean or sterilize.

BRIEF DESCRIPTION OF THE DRAWINGS

FIG. 3B is an enlarged exploded view the parts of the Rongeur.

FIG. 4 is a perspective view of the push button actuator of the Rongeur.

FIG. 5 is a cross sectional view of the push button actuator in the Rongeur.

DETAILED DESCRIPTION OF THE INVENTION

Figure 1:
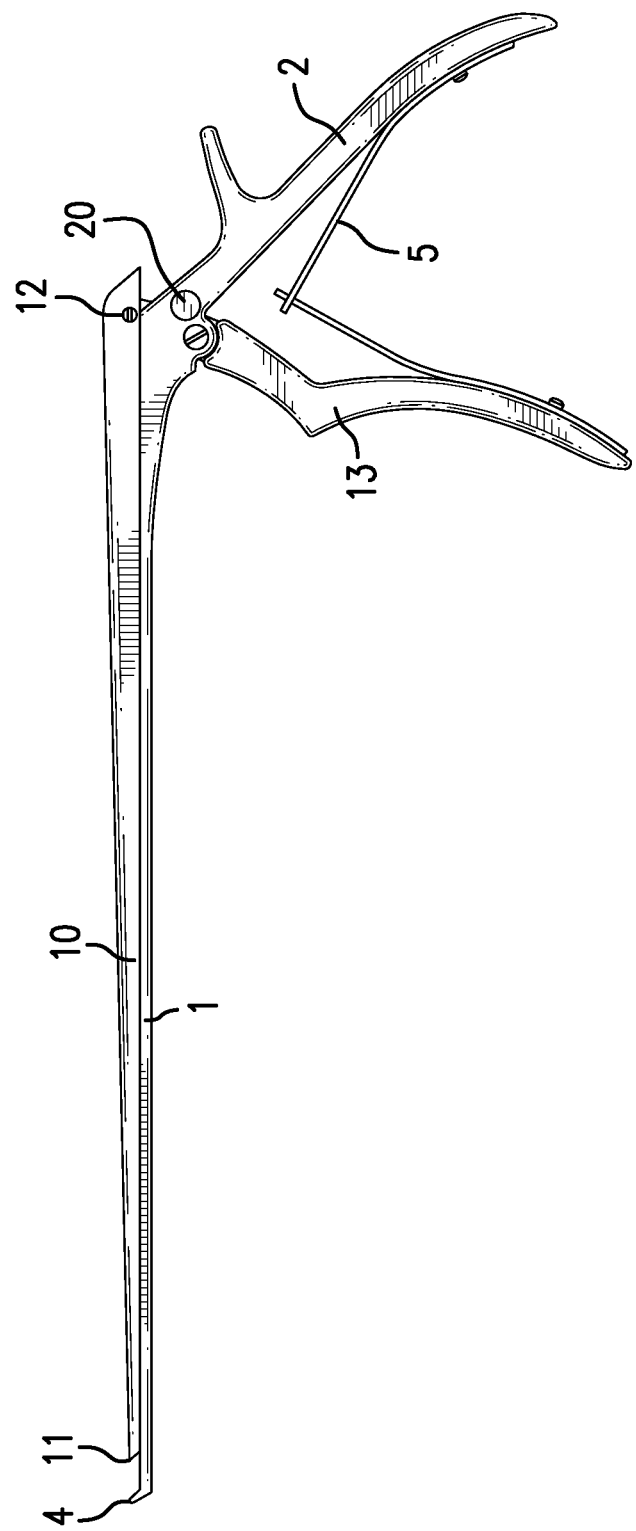
FIG. 1 is a perspective view of the Rongeur in cutting position ready for use.
Figure 2A:
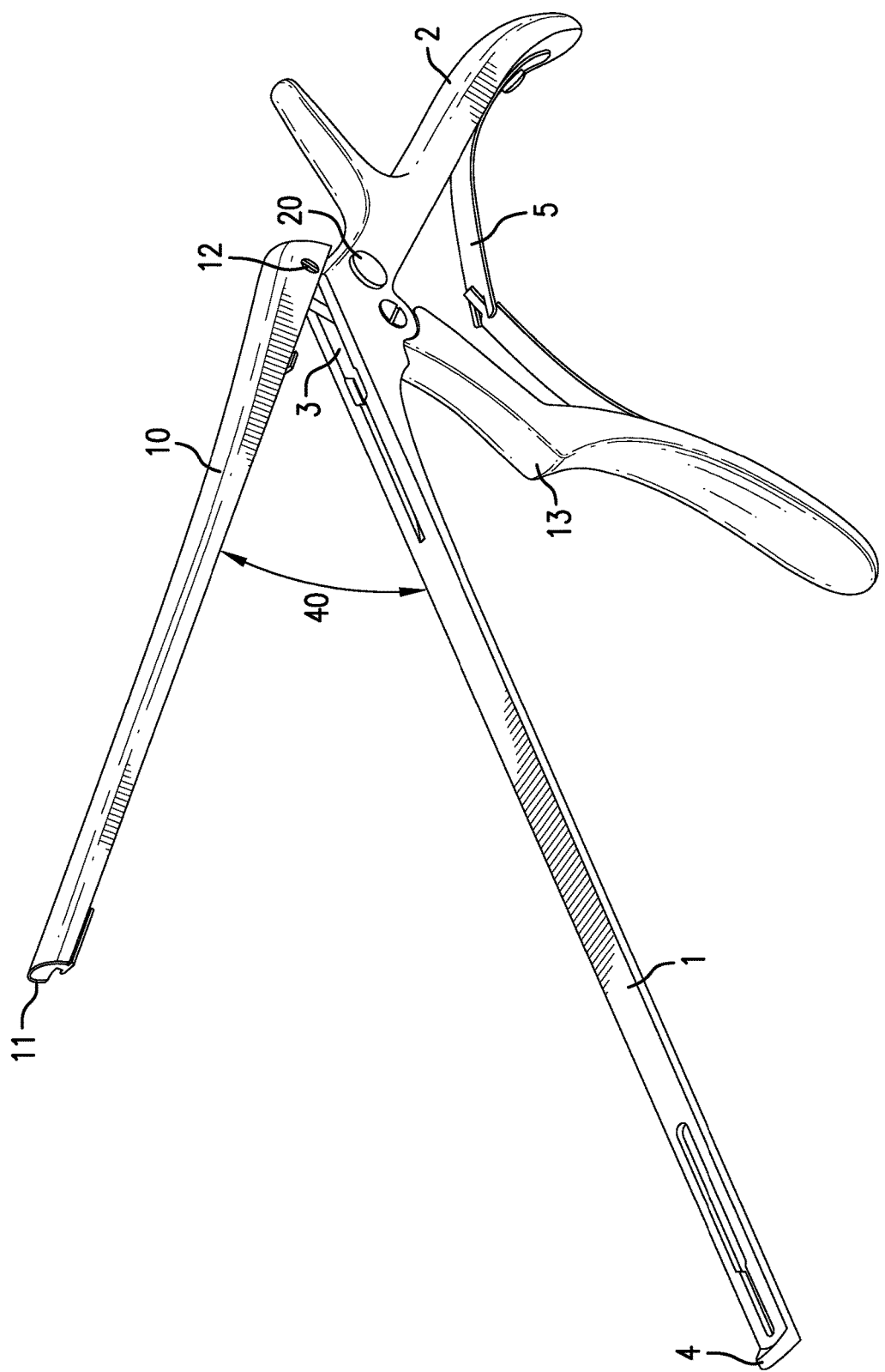
FIG. 2A is a perspective view of the Rongeur with the moveable top shaft separated at an acute angle from the fixed bottom shaft and ready for cleaning.

FIG. 1 shows a preferred embodiment of the disclosed invention in which top shaft (10) is in a normal cutting position relative to fixed bottom shaft (1), ready for use. Top shaft (10) is slideably connected to, and axially aligned with fixed bottom shaft (1). Top shaft (10) has a proximal end with a cutting edge (11) and a distal end containing a cavity (9) (shown in FIG. 2B) orthogonally transversed by drive pin (12). Fixed bottom shaft (1) has a proximal end with a foot plate (4) and a distal end forming rear handle (2). At the transition of bottom shaft (1) to rear handle (2) lies the interaction of front handle (13) with fixed bottom shaft (1) and push button actuator (20). Front handle (13) is pivotally attached to rear handle (2) and is held in the open or normal position by lever spring (5). Lever spring (5) resists against the compression of front handle (13) toward rear handle (2) and keeps the Rongeur in normal position. Top shaft (10), when slidingly engaged with fixed bottom shaft (1) as shown in FIG. 1, may be retracted slightly by depressing the push button actuator (20) which allows the separation of top shaft (10) from fixed bottom shaft (1) to at least an acute angle (40) (shown in FIG. 2A). Also shown in FIG. 2A, is slot (3) which is medially centered on fixed bottom shaft (1) at its transition to rear handle (2). The separation of top shaft (10) from fixed bottom shaft (1) at angle (40) allows direct access to all surfaces of the long parts of the Rongeur for cleaning and sterilization. Once cleaning and sterilization occurs, simply returning top shaft (10) to slideable connection with fixed bottom shaft (1) returns Rongeur to fully operable condition and ready for the next use.

Figure 2B:
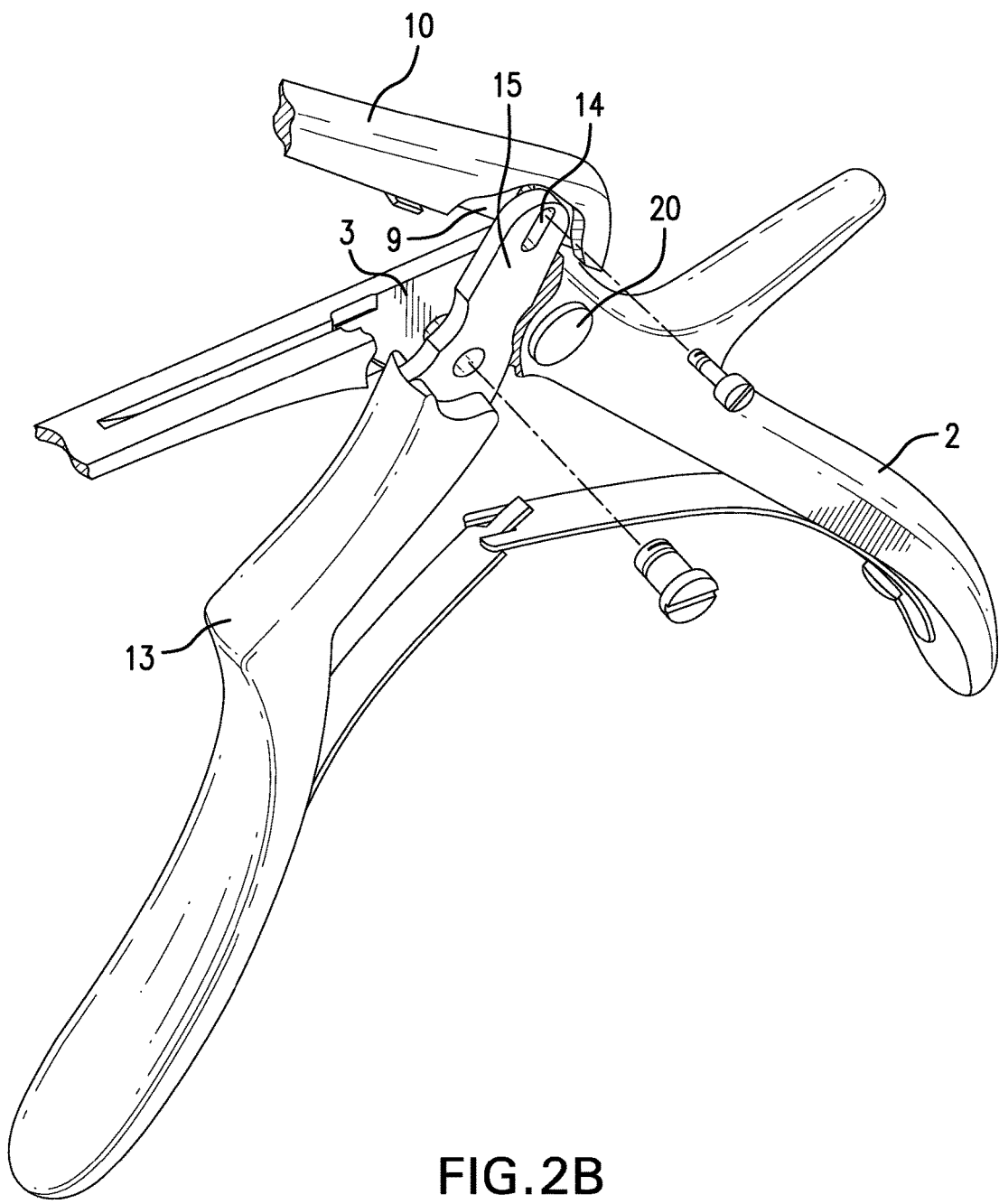
FIG. 2B is a cut away view of the cavity of the proximal end of the moveable top shaft of the Rongeur and of the slot of the fixed bottom shaft where it interacts with the front handle.
Figure 3A:
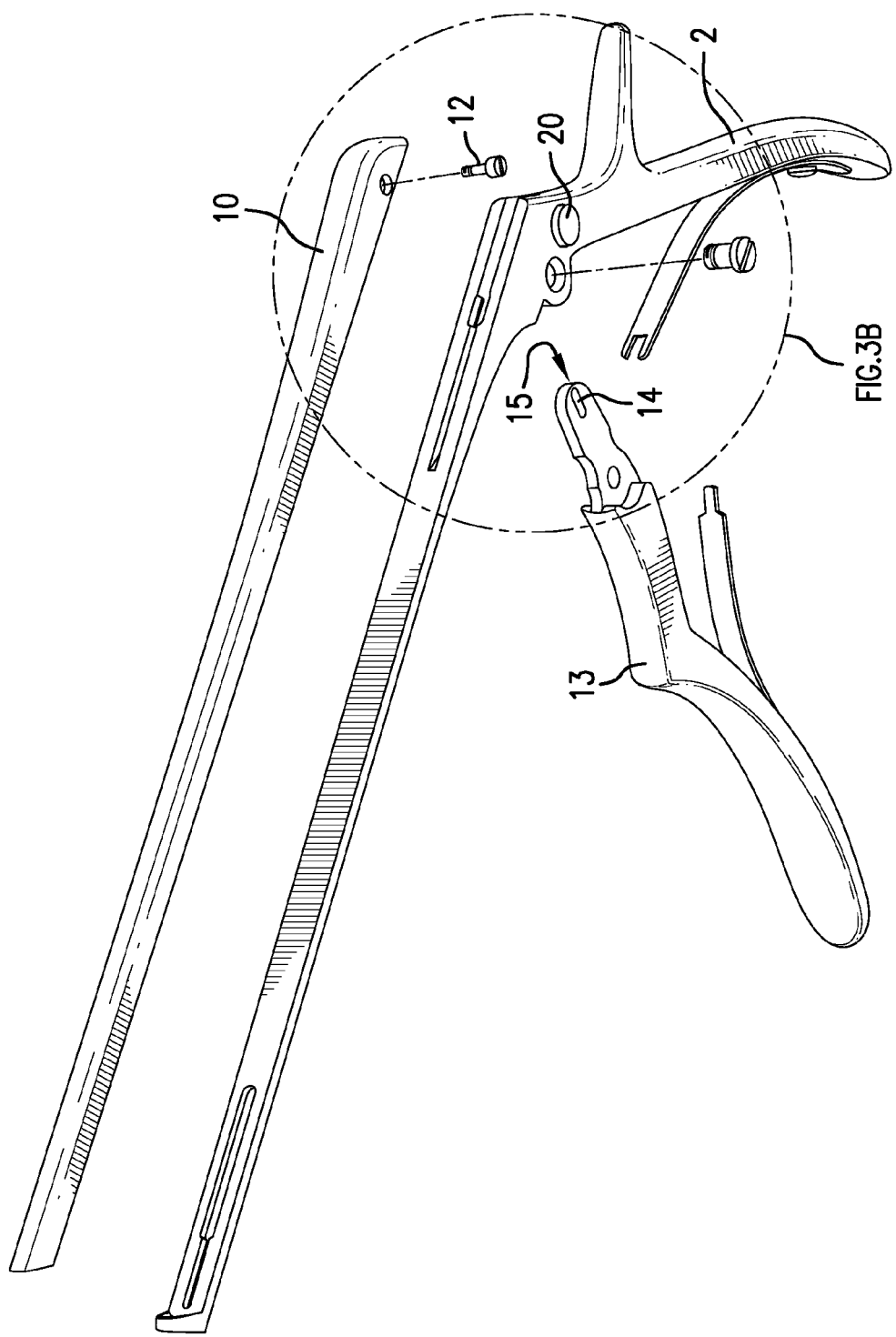
FIG. 3A is an exploded view of the parts of the Rongeur.

Depicted in FIG. 3A, front handle (13) has a proximal end (15) containing drive hole (14) and a distal end forming front handle (13) of the Rongeur. Turning to FIG. 2B, the proximal end (15) of front handle (13) is fitted through slot (3) of fixed bottom shaft (1) and into cavity (9) of top shaft (10) whereby drive hole (14) receives drive pin (12). In this simple design, once the Rongeur is assembled, drive pin (12) is never released from drive hole (14) during the use of the Rongeur in a medical procedure or thereafter in an activated position during cleaning and sterilization. FIGS. 3A and 3B further show the parts of the push button Rongeur. The proximal end (15) of front handle (13) has rear surface (16) which contacts actuator shaft (23) (shown in FIG. 4) when the push button actuator (20) is in normal position and ready for use.

FIG. 4 shows the structure of push button actuator (20). Push button actuator (20) is comprised of a compression spring (21) and shaft (23) containing groove (22).

Shown in FIG. 5 is a cross section of the push button actuator (20) in normal position before actuation. The push button actuator (20) is operably connected to fixed bottom shaft (1). Compression spring 21 has a distal end (28) attached to an inner wall in slot (3) of fixed bottom shaft (1) and a proximal end (29) contacting push button actuator (20). Before activation, compression spring (21) is extended holding push button actuator (20) in its normal position. Push button actuator (20) is depressed to an activated position (not shown) by pushing push button actuator (20) toward fixed bottom shaft (1) [the direction shown by arrow (25)], thereby compressing compression spring (21). On actuation of push button actuator (20), rear surface (16) of front handle (13) (FIG. 3B) slips into groove (22), thereby allowing top shaft (10), which is engaged with drive pin (12) through drive hole (14) in the proximal end of front handle (13), to be slightly retracted from the outer circumference of shaft (23), to contact the surface of groove (22). Top shaft (10) may then be separated from fixed bottom shaft (1) to an angle (40) (shown in FIG. 2). The separation of top shaft (10) from fixed bottom shaft (1) to angle (40) makes the parts of the Rongeur readily accessible for cleaning and sterilization. This separation of the long parts to angle (40) is facilitated by the movement of drive pin (12) within drive hole (14) which is elongated to accommodate the movement of drive pin (12). Drive pin (12) remains captured by drive hole (14) at all times while the Rongeur is in use and while is long parts are separated for cleaning.

After cleaning, top shaft (10) is returned to contact with fixed bottom shaft (1), compression spring (21) returns push button actuator (20) to its normal position, and the Rongeur is ready for use (FIG. 1). When ready for use, top shaft (10) is slideably connected to fixed bottom shaft (1) and held in a forward position by the contact of rear surface (16) of front handle (13) (FIG. 3B) with shaft (23) of push button activator (20) (FIGS. 4 and 5).

The foregoing detail of the disclosed embodiment of the push button Rongeur is not intended as a limitation on other configurations of the push button actuator which may be apparent to those skilled in the art without departing from the scope and spirit of the disclosed invention as defined in the following claims.

What is claimed is:

1. A Rongeur comprising:
 a top shaft having a proximal end and a distal end, the top shaft proximal end having a cutting edge, and the top shaft distal end defining a cavity;
 the top shaft slidably connected to a fixed bottom shaft having a proximal end and a distal end, the bottom shaft proximal end having a foot plate, and the bottom shaft distal end defining a slot and transitioning into a fixed rear handle;
 a front handle having a distal end and a proximal end, the front handle distal end defining a handle pivotally connected to the fixed bottom shaft, and the front handle proximal end fitted through the slot and into the cavity;
 the front handle proximal end and the top shaft distal end comprising a drive pin and drive hole assembly, the drive pin received in the drive hole such that the top shaft distal end is pivotally connected to the drive pin and drive hole assembly;
 a push button actuator operably connected to the fixed bottom shaft and in contact with a rear surface of the front handle proximal end, the push button actuator having an outer circumference and a groove;
 wherein in a normal position the front handle rear surface contacts the push button actuator outer circumference, thereby limiting the retraction of the top shaft; and upon depression of the push button actuator to an activated positon, the front handle rear surface contacts the push button actuator groove, thereby allowing the top shaft to retract, separate from the fixed bottom shaft, and pivot at the drive pin and drive hole assembly to at least an acute angle, exposing the Rongeur for thorough cleaning and sterilization.

2. The Rongeur of claim 1, wherein the cavity is orthogonally transversed by the drive pin.

3. The Rongeur of claim 1, wherein the front handle proximal end defines the drive hole.

4. The Rongeur of claim 1, wherein the drive hole is elongated to allow movement of the drive pin.

5. The Rongeur of claim 1, wherein the slot is medially centered in the fixed bottom shaft.

6. The Rongeur of claim 1, wherein the drive hole completely encloses an outer surface of the drive pin.

7. The Rongeur of claim 1, wherein the push button actuator further comprises a compression spring biasing the push button actuator in the normal position.

8. The Rongeur of claim 1, wherein closing the top shaft at the drive pin and drive hole assembly, slidably reconnecting the top shaft to the fixed bottom shaft, and engaging the front handle to slide the top shaft cutting edge toward the bottom shaft foot, returns the push button actuator to the normal position, such that the front handle rear surface contacts the push button actuator outer circumference.

9. The Rongeur of claim 1, further comprising a lever spring engaged to the front handle and the rear handle, biasing the front handle away from the rear handle.

* * * * *